United States Patent [19]

Swartz

[11] Patent Number: 4,870,969
[45] Date of Patent: Oct. 3, 1989

[54] ELECTRODE APPLICATION SYSTEM AND METHOD FOR ELECTROCONVULSIVE THERAPY

[75] Inventor: Conrad M. Swartz, Lake Forest, Ill.

[73] Assignee: Somatics, Inc., Lake Bluff, Ill.

[21] Appl. No.: 245,355

[22] Filed: Sep. 16, 1988

[51] Int. Cl.[4] .............................................. A61N 1/38
[52] U.S. Cl. .................................. 128/419 S; 128/798
[58] Field of Search .................. 128/419 S, 640, 798, 128/802, 803

[56] References Cited

U.S. PATENT DOCUMENTS

| | | | |
|---|---|---|---|
| 4,243,052 | 1/1981 | Bailey | 128/798 |
| 4,391,278 | 7/1983 | Cahalan et al. | 128/640 |
| 4,422,461 | 12/1983 | Glumec | 128/802 X |
| 4,509,535 | 4/1985 | Bryan | 128/798 |
| 4,524,087 | 6/1985 | Engel | 128/798 X |
| 4,708,149 | 11/1987 | Axelgaard et al. | 128/798 |
| 4,709,700 | 12/1987 | Hyrman | 128/419 S |

FOREIGN PATENT DOCUMENTS 0226568  6/1987  European Pat. Off. ............ 128/798

OTHER PUBLICATIONS

Finlay et al., "Controlled Voltages . . . Therapy", MED. Inst., vol. 12, No. 2, Mar.–Apr. 1978, pp. 83–87.

Primary Examiner—Lee S. Cohen
Attorney, Agent, or Firm—Eliot S. Gerber

[57] ABSTRACT

A medical method and system in electroconvulsive therapy (ECT) uses a disposable electrode, which does not use a liquid, such as conductive gel or saline solution. The electrode is a flexible multi-layer pad having an adhesive surface which is covered by a removable cover sheet. The pad comprises a layer of adhesive non-liquid conductive hydrogel, a thin conductive plastic film layer, a conductive metal foil layer connected to a wire lead, and an insulative plastic layer, preferably a plastic foam.

7 Claims, 1 Drawing Sheet

ELECTRODE APPLICATION SYSTEM AND METHOD FOR ELECTROCONVULSIVE THERAPY

BACKGROUND OF THE INVENTION

1. Field of the Invention

The present invention relates to medicine and more particularly to the use of electrodes applied to the skin of the patient in electroconvulsive therapy (ECT).

2. Description of the Related Art

Electroconvulsive therapy ("ECT"), sometimes called "shock therapy", is used to treat major depression. A report of a NIMH panel (National Institute of Mental Health), reported in *Science* (June 28, 1985, pg. 1510, 1511), concluded that "not a single controlled study has shown another form of treatment to be superior to ECT in the short-term management of severe depressions." The *Science* article noted that the complication rate is about 1 in 1700 treatments and severe and prolonged memory loss is extremely rare, and possibly non-existent.

In an ECT treatment, two electrodes are applied to the skin of the patient, at the head, and a small electric current passes through the electrodes. Only a small portion of the current reaches the brain as the rest is deflected by the skin and skull. The current excites neural tissue, triggering a seizure which resembles, on an EEG display (electroencephalograph) the seizures of epilepsy.

In the "Thymatron" ECT instrument (TM of Somatics, Inc., Lake Bluff, Ill.), the stimulus is a brief series of electrical square waves. The stimulus is a constant current of 0.9 amps limited to 450 volts, consisting of 140 bipolar pulses per second of 1 msec. width, which is adjustable 0.2–4.0 seconds in duration.

At the present time, the electrodes that are used in ECT are flat or concave metal disks that are reusable. The metal disk, if simply held on the skin, would present too great an electrical impedance. The skin may be, for example, the skin of the scalp or forehead. The impedance is reduced to an acceptable level by using a conductive gel or a conductive saline (salt) solution pad.

However, both the gel and the saline pad present serious problems.

The gel used is a thick, viscous conductive aqueous gel. The metal disk electrodes are covered with the thick gel. The electrodes are held on the skin of the patient by pressure from a perforated rubber headstrap or from electrically insulated handles held by a therapist. The viscous gel remains on the skin after the metal electrodes are removed and the gel should then be removed. However, sometimes the gel is not fully removed from the skin, scalp, or hair after the ECT treatment. The crusted gel residue may compromise the confidentiality of the ECT treatment, and some patients find its presence aesthetically displeasing.

As an alternative to conductive gel, disk electrodes are sometimes covered with saline (salt) soaked pads to reduce the skinelectrode electrical impedance. However, the saline eventually corrodes the metal electrodes and their wire leads, reducing and ultimately blocking the electrical stimulus. The failure of the electrodes, due to corrosion, is unpredictable as the corrosion may be hidden. Any excess of saline that leaks out of the pads may create an electrical short circuit between the electrodes. Such short circuits may not be noticed and yet may prevent delivery of the full electrical stimulus to the patient's brain.

The use of gel or saline solution, with metal electrode disks, presents other disadvantages. First, frequently the metal disk electrodes, whether flat or concave, fail to closely conform to the anatomical topography of the region of the patient's head. The patient's head may be more curved, or less curved, than the face of the electrode. Such incomplete contact reduces the contact area and increases the possibility of slippage and skin burn. Secondly, therapists, and anesthetists who administer ECT, repeatedly come in contact with the patient's head during treatment. They may accidentally touch the conductive surfaces of the electrode disks, receiving an electrical shock, which is painful and may be dangerous, for example, if the shock crosses the heart. Thirdly, the disks must be carefully washed between uses, to remove the gel or saline residue and prevent contamination, and possible infection, of one patient by another. Fourthly, the disk electrodes are subject to corrosion from incompletely removed gel or saline solution, and they may be damaged if dropped or mishandled.

Often the disk electrodes are held to the patient's head by an elastic headband. Some patients object to the sensation of continuous pressure on their temples when a rubber headband (headstrap), with metal electrode assembly, is tightened on their head. Such headstraps, and electrode assemblies, are subject to breakage and loss.

SUMMARY OF THE INVENTION

In accordance with the present invention, a method is provided for electroconvulsive therapy (ECT) in which electrical stimulus is applied to the skin of a patient through electrodes which are flexible, single-use and disposable.

Each electrode has a removable connector plug, preferably a "banana" female connector, and a tinsel wire lead. The wire is electrically connected to the metal foil of a flexible electrode. The electrode is a flat and thin multi-layer structure which, starting at the back, consists of the following layers which are laminated together: A back layer of insulative polyethylene foam, a metal foil, a plastic insulative layer, a conductive adhesive layer and a cover sheet.

In use, the cover sheet is removed, the adhesive layer is pressed onto the skin of the patient, the connector plug is connected to the ECT instrument, the patient receives the electrical impulses through the electrode, the connectors are unplugged and the adhesive electrode is pulled off the skin of the patient.

As no fluid gels or solutions are employed, there is no leakage. The electrodes are used only once, so there is no danger of contamination between patients or corrosion of the electrodes. The adhesive adheres the electrode to the correct location, without slippage, so there is no danger of burn to the patient or electrical shock to the therapist. The electrode comes off the skin cleanly, without leaving a residue, so there is no loss of confidentiality or stains due to a residue.

OBJECTIVES AND FEATURES OF THE INVENTION

It is an objective of the present invention to provide a method, in ECT, of easily, quickly and firmly securing an electrode to a patient without using a gel or other fluid.

It is a further objective of the present invention that the electrode may be accurately placed on the skin of the patient, in the desired location, and will not slip or otherwise become dislodged during the treatment.

It is a further objective of the present invention that there is no danger of shock from the electrode to those providing the treatment.

It is a further objective of the present invention that the electrode may rapidly and easily be removed by peeling it off, without washing the patient, and yet will not leave a residue showing that an electrode had been applied.

It is a further objective of the present invention that the electrode may be used only once, and then disposed of, so there is no danger of contamination from patient-to-patient and so that corrosion is not a problem.

It is a further objective of the present invention that a headstrap or electrode handle is not required.

It is a further objective of the present invention that good contact, and low impedance, is obtained because the electrode conforms to the shape of the patient's head in the area to which it is applied.

BRIEF DESCRIPTION OF THE DRAWINGS

Other objectives and features of the present invention will be apparent from the following detailed description of the preferred embodiment, taken in conjunction with the accompanying drawing.

In the drawing.

DESCRIPTION OF THE PREFERRED EMBODIMENT

Figure 1:
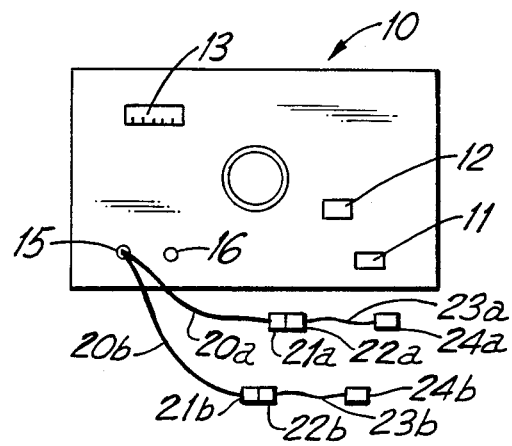
FIG. 1 is a block-schematic diagram of the system using the method of the present invention.
Figure 2:
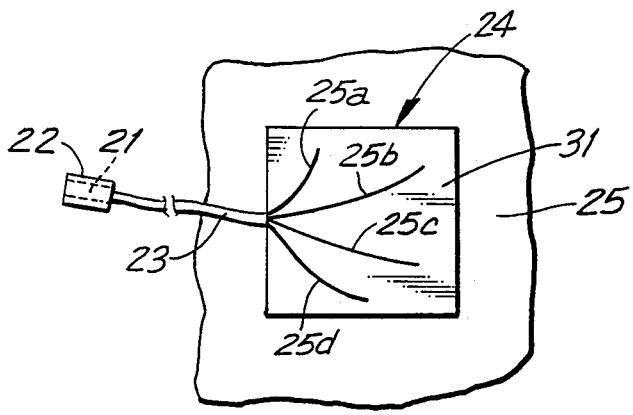
FIG. 2 is a top plan view of one embodiment of the electrode used in the system of FIG. 1 showing the metal foil layer.
Figure 3:
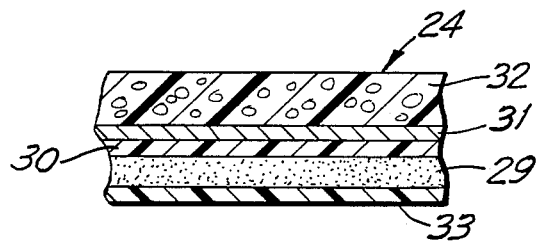
FIG. 3 is a side view, partly in cross-section, of the electrode used in the present invention.

As shown in FIG. 1, the method of the present invention is used in electroconvulsive therapy (ECT). The ECT instrument 10 has controls for power 11 (on-off), the start of the treatment ("treat 12"), a light-emitting dial showing impedance ("impedance 13") to determine if the electrodes are properly attached, a selection dial to select the percent of energy ("% energy 14") and automatically deliver the recommended dose of electricity, jacks for the ECT output ("ECT 15") and EEG recording ("EEG 16"). The outputs of the ECT instrument 10, on lines 20a, 20b, are to the male banana connector plugs 21a, 21b which removably fit with female banana connector plugs 22a, 22b. The connector plugs 22a,22b are electrically connected to wires 23a, 23b which lead to the electrode pads 24a, 24b. Preferably the wires 23a, 23b are white tinsel wires. As shown in FIG. 2, the electrode 24 is adhered to the skin 25 of a patient, for example, at the scalp.

When properly inserted, the entire outer conducting surface of the male banana connector plug 21 is covered by the outer barrel of the female receptacle plug 22 so that there is no exposed conducting surface at the connector.

The wire 23 is attached at one end to the multilayered electrode pad 24 and, at its opposite end, to the plug connector, preferably a 4 mm insulated banana female plug. The wire 23 may be of any length, but a convenient length is about two feet. The wire 23 has an outer electrically insulating cover, for example, polyvinyl chloride. Inside, the wire 23 has at least one metal strand; but more than one strand improves the reliability of the electrical conduction between the lead and the electrode, so preferably four strands are used.

The end of the wire lead is stripped bare, i.e., its cover removed, and its strands 25a–25d are distributed over the metal foil 31 of the electrode pad 24. The electrode pad 24 comprises four flat and flexible layers, each of which has the same area and shape. The layers are laminated together to form a flexible and unitary pad. The innermost layer 29, which contacts and adheres to the patient's skin, is a conductive and flexible adhesive, preferably hypoallergenic hydrogel. The adhesive layer 29 may be of any suitable thickness, preferably 0.030 inch, i.e., (30 mils). The next layer is a flexible conductive plastic film layer 30 which is laminated to a flexible metal foil conductive layer 31. The foil 31, preferably aluminum foil, distributes the electrical stimulus over the entire surface of the hydrogel layer 29. The foil 31 prevents concentration of electrical current through the hydrogel from just those areas close to the lead wires. The high current densities that would result in the absence of distribution of the electricity over the entire surface of the adhesive layer 29 would increase the possibility of skin burn.

The outer layer 32 is of flexible electrically insulating material, preferably polyethylene foam, which may be of any suitable thickness, preferably 1/32". The adhesive layer 29 is covered by a removable cover sheet 33, preferably a flexible plastic film such as Mylar (TM of Dow) of 0.005-inch thickness (5 mils).

The shape in the plane of the multilayered electrode pad may be of any configuration, such as elliptical, circular or rectangular. In FIG. 2 a rectangular pad 24 is adhered to skin 25. The total surface of the pad 24 should be at least 0.7 in$^2$. The preferred surface area is between 3 in$^2$ and 5 in$^2$, to disperse any heat generated at the contact of the pad with the skin. The pad is sufficiently large to prevent skin burn. A preferred shape is approximately a rectangle with rounded corners whose size is 1.625"×2.125".

In use, before the electrode pad 24 is applied, the skin of the patient, at the site of the pad, is cleaned. It is customary, and good clinical practice, for the therapist to clean and dry the patient's skin prior to application of the electrode, to remove oils, crusts, and skin contaminants. In this cleansing, a grease solvent such as ethyl acetate is preferably employed. Any thick hair at the electrode pad site should be shaved off. Once the skin is suitably prepared, the adhesive layer is exposed by peeling off the cover sheet, and the adhesive layer of the pad is pressed on the patient's skin, to which it adheres.

Stimulus electrodes are used in pairs with ECT. In customary clinical practice, one electrode is applied to the skin of the patient over the temporalis muscle (i.e., the temple) on either the right side or the left side of the face. The other electrode can be applied in any of a number of sites, including: over the other temporalis muscle, over the scalp at the vertex or just lateral to it, or over the scalp just to the rear and above the ear. The site location is chosen according to the discretion of the treating physician. When the skin is properly prepared, the multilayered electrode pad 24 may be used with any placement of electrodes on the patient's head. It is also feasible to apply one multilayer electrode pad 24 to one application site and use the usual metal disk electrode on another application site.

I claim:

1. The system in electroconvulsive therapy (ECT) including:
   an ECT instrument means which, under operator control, produces a burst of electrical waves sufficient to induce a seizure in the brain of a human patient;
   a one-use disposable connector-pad assembly comprising a connector plug portion removably electrically connected to said ECT instrument means, a flexible multi-layer laminated electrode pad and a wire connected to said plug portion; said pad applying said electrical waves to the skin of the patient and including an adhesive conductive layer which is a plastic conductive film having first and second surfaces, a metal foil layer electrically connected to said wire and covering said adhesive layer second surface, an insulative layer covering said metal foil layer; and a cover layer removably covering said adhesive layer first surface; wherein said wire is a multi-strand wire of at least three metal strands and said strands at their ends are separated, extend across and are electrically connected to the said metal foil layer.

2. The ECT system of claim 1 wherein said insulative layer is a plastic film.

3. The ECT system of claim 1 wherein said foil is aluminum foil.

4. The ECT system of claim 1 wherein said adhesive layer is a non-flowing electrolyte low impedance hydrogel.

5. The ECT system of claim 1 wherein said cover layer is a plastic film.

6. The ECT system of claim 1 and including an output wire connected to said ECT instrument means, and a second plug portion connected to said output wire and removably plugged into said plug portion of said connector-pad assembly.

7. The method, in electroconvulsive therapy, using an ECT instrument, of stimulating the brain of a patient with electrical energy of high current density sufficient to induce seizure in the patient, including the steps of:
   forming a pad assembly by laminating together a conductive adhesive layer of a plastic conductive film and having a first and a second surface, a flexible conductive metal foil layer covering said second surface having spread across said foil a plurality of at least three separated strands of multi-strand wire, and an insulative layer covering the metal foil layer, said pad assembly having a cover sheet removably covering said first surface; joining the wire at its end opposite the foil layer to an electrical connector plug;
   arranging the patient for the therapy, removing the cover sheet from the adhesive layer;
   adhering the adhesive layer to the skin of the patient at the head, connecting the connector plug to the ECT instrument;
   treating the patient by applying electric current to the head of the patient from the ECT instrument through the adhesive layer, foil layer, multi-strand wire, and the connector plug; and
   after said treatment peeling the adhesive layer from the skin and disposing of the cover sheet and the pad assembly.

* * * * *